United States Patent [19]

Degen et al.

[11] Patent Number: 5,364,972
[45] Date of Patent: Nov. 15, 1994

[54] PREPARATION OF NITROBENZOPHENONES, AND A COLOR-STABLE MODIFICATION OF A BENZOPHENONE-AZOPYRIDONE DYE

[75] Inventors: Helmut Degen, Frankenthal; Norbert Zimmerman, Waldsee, both of Germany; Ralf Brueckmann, Charlotte, N.C.; Gunther Lamm, Hassloch, Germany; Arno Lange, Bad Duerkheim, Germany; Helmut Reichelt, Neustadt, Germany

[73] Assignee: BASF Aktiengesellschaft, Ludwigshafen, Germany

[21] Appl. No.: 948,579

[22] Filed: Sep. 23, 1992

[30] Foreign Application Priority Data

Sep. 25, 1991 [DE] Germany ............... 4131844

[51] Int. Cl.$^5$ ............................................. C07C 45/45
[52] U.S. Cl. ..................................... 568/306; 568/323
[58] Field of Search .................... 568/319, 306, 323

[56] References Cited

U.S. PATENT DOCUMENTS

| | | |
|---|---|---|
| 2,007,382 | 7/1935 | Ockman et al. |
| 4,153,632 | 5/1979 | Padmanathan ............. 568/306 |
| 4,374,640 | 2/1983 | Tappe et al. |
| 4,413,144 | 11/1983 | Tappe et al. ............. 568/306 |
| 4,629,811 | 12/1986 | Dominianni |
| 4,777,300 | 10/1988 | Colquhoun et al. ............. 568/319 |

FOREIGN PATENT DOCUMENTS

| | | |
|---|---|---|
| 66153 | 12/1982 | European Pat. Off. |
| 0068186 | 1/1983 | European Pat. Off. |
| 0093590 | 11/1983 | European Pat. Off. |
| 463401 | 1/1992 | European Pat. Off. |
| 2076138 | 10/1971 | France |
| 2160583 | 6/1973 | France |
| 2170223 | 9/1973 | France |
| 2157229 | 5/1973 | Germany |
| 2201208 | 8/1973 | Germany |
| 1272043 | 4/1972 | United Kingdom |
| 1360749 | 7/1974 | United Kingdom |
| 1410542 | 10/1975 | United Kingdom |
| 430631 | 1/1976 | U.S.S.R. |
| 654603 | 3/1979 | U.S.S.R. ............. 568/306 |

OTHER PUBLICATIONS

Chemical Abstracts, Band 101, Nr. 18, 29, Oct. 1984, p. 79, Zusammenfassung Nr. 153476p, Columbus, Ohio, US; & JP-A-5 996 168 (Mitsubishi) Jun. 2, 1984*Zusammenfassung*.

Chemical Abstracts, vol. 84, 1976, Columbus, Ohio, US; abstract No. 105291h, Farberov, M. I. Et al. '6-or 7-Aminoanthraquinone-2-carboxylic acids,' SU-A-430 631 Jan. 5, 1976, 1 page.

J. Org. Chem., vol. 54, No. 14, 1989, pp. 3478–3482.

*Primary Examiner*—James H. Reamer
*Attorney, Agent, or Firm*—Oblon, Spivak, McClelland, Maier & Neustadt

[57] ABSTRACT

A process for preparing nitrobenzophenones by reaction of benzene or its derivatives with nitrobenzoyl chloride in the presence of a Lewis acid, a color-stable modification of 1,4-dimethyl-5-cyano-3-[4-(2,4-dimethylbenzoyl)phenylazo]-2-hydroxy-6-pyridone and its use for dyeing or printing synthetic fiber material are described.

11 Claims, No Drawings

PREPARATION OF NITROBENZOPHENONES, AND A COLOR-STABLE MODIFICATION OF A BENZOPHENONE-AZOPYRIDONE DYE

The present invention relates to a novel process for preparing nitrobenzophenones by reacting benzene or its derivatives with nitrobenzoyl chloride in the presence of a Lewis acid, to a color-stable modification of 1,4-dimethyl-5-cyano-3-[4-(2,4-dimethylbenzoyl)-phenylazo]-2-hydroxy-6-pyridone and to the use thereof for dyeing or printing synthetic fiber material.

The preparation of nitrobenzophenones by reacting nitrobenzoyl chloride with benzene or its derivatives in a Friedel-Crafts reaction is known. For example, EP-A 66153 describes the synthesis of 4-nitro-4'-isopropylbenzophenone using chlorobenzene or dichloroethane as inert solvent. However, these solvents, as well as others, eg. nitrobenzene, which are conventionally used for this type of reaction, pollute the waste water.

Furthermore, SU-A 430 631 describes the preparation of 4-nitro-2',4'-dimethylbenzophenone by reacting p-nitrobenzoyl chloride with a 3-molar excess of m-xylene in the presence of iron chloride at 150° C. However, the benzophenone yield is unsatisfactory.

Finally, DE-A 2 201 208 discloses a process in which p-nitrobenzoyl chloride is reacted with m-xylene or anisole in each case in the absence of inert organic solvents in the presence of 2,4,6-trinitrobenzenesulfonic acid as catalyst. The molar ratio of benzene derivative to p-nitrobenzoyl chloride in this case is 1.5:1. However, the disadvantages of this process are the high reaction temperature and the unsatisfactory yield of required product.

It is an object of the present invention to provide a novel process for preparing nitrobenzophenones which is based on Friedel-Crafts acylation but in which the abovementioned disadvantages are avoided. The novel process ought also to be simple to carry out industrially and to provide the required products in high yield and purity.

We have found that this object is achieved by preparing nitrobenzophenones of the formula I

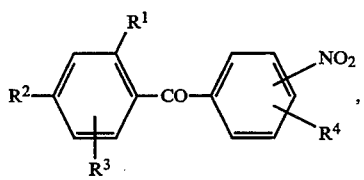

where $R^1$, $R^2$ and $R^3$ are identical or different and each, independently of one another, is hydrogen, $C_1$-$C_6$-alkyl or cyclohexyl and $R^4$ is hydrogen or halogen, by reacting aromatic compounds of the formula II

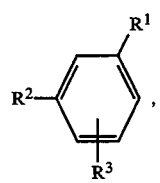

where $R^1$, $R^2$ and $R^3$ each have the abovementioned meanings, with nitrobenzoyl chlorides of the formula III

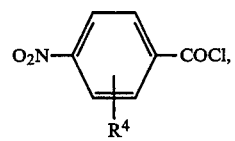

where $R^4$ has the abovementioned meanings, in the presence of a Lewis acid, in a process wherein the reaction is carried out essentially in the absence of inert solvents at from 50° to 110° C. and with a molar ratio of aromatic compound of the formula II to nitrobenzoyl chloride III of from 1:1 to 2:1, and catalytic amounts of aluminum chloride or iron(III) chloride are used as Lewis acid.

Examples of $R^1$, $R^2$ and $R^3$ in formula I are methyl, ethyl, propyl, isopropyl, butyl, isobutyl, sec-butyl, tert-butyl, pentyl, isopentyl, neopentyl, tert-pentyl, hexyl and 2-methylpentyl.

Suitable examples of halogen for $R^4$ are chlorine and bromine.

Examples of aromatic compounds of the formula II suitable for the process according to the invention are benzene, toluene, o-, m- or p-xylene, 1,2,4-trimethylbenzene, ethylbenzene, 3-ethyltoluene, isopropylbenzene, m-diisopropylbenzene, isobutylbenzene, sec-butylbenzene, tert-butylbenzene, m-diisobutylbenzene, hexylbenzene or cyclohexylbenzene.

A procedure in which an aromatic compound of the formula IIa

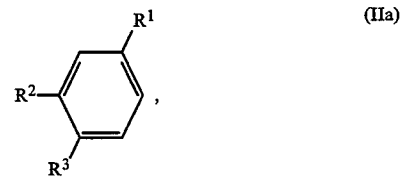

where $R^1$, $R^2$ and $R^3$ each have the abovementioned meanings, is used as starting material is emphasized.

A procedure in which $R^1$ and $R^2$ in formula II are each $C_1$-$C_4$-alkyl, especially methyl, and $R^3$ is hydrogen, is preferred.

Examples of suitable nitrobenzoyl chlorides III are o-, m- or p-nitrobenzoyl chloride and 3-nitro-4-chlorobenzoyl chloride, with the use of m- or p-nitrobenzoyl chloride being preferred and use of p-nitrobenzoyl chloride being particularly preferred.

As mentioned above, suitable Lewis acids are aluminum chloride or iron(III) chloride, with the use of iron(III) chloride being preferred. It is also possible to employ iron(III) oxide, which is converted into iron(III) chloride by the hydrogen chloride produced during the reaction.

The molar ratio of aromatic compound II to nitrobenzoyl chloride is usually from 1:1 to 2:1, preferably from 1.1:1 to 1.3:1.

As mentioned above, the Lewis acid is added in catalytic amounts which means, for example, from 0.5 to 20% by weight, preferably from 2 to 8% by weight, of Lewis acid based on the aromatic compound II.

The process of the invention is essentially carried out in the absence of inert solvents, i.e. usually in the complete absence thereof, but the presence of up to 10% by weight, preferably up to 5% by weight, in each case based on the weight of the aromatic compound II, of an inert solvent is also possible.

Examples of suitable inert solvents are chlorobenzene, dichlorobenzene and nitrobenzene.

The process according to the invention is expediently carried out in such a way that a mixture of aromatic compound II, nitrobenzoyl chloride III and Lewis acid is prepared and heated to from 50° to 110° C., preferably from 50° to 90° C., and then stirred at this temperature for, in general, from 3 to 6 hours.

The hydrogen chloride formed in the acylation is continuously removed from the mixture throughout the reaction.

After the reaction is complete it is possible, where appropriate, to remove and recover excess aromatic compound of the formula II by steam distillation. The resulting nitrobenzophenone of the formula I can be used directly for subsequent reactions.

A particularly advantageous variant starts from nitrobenzoic acid which is converted into nitrobenzoyl chloride in situ. In this case the nitrobenzoic acid is suspended in the aromatic compound II in the abovementioned molar ratio (of aromatic compound II to nitrobenzoyl chloride III). Any water introduced with the acid can be removed by azeotropic distillation.

From 1 to 1.1 mol of thionyl chloride per mol of nitrobenzoic acid is added to the resulting suspension at from 60° to 100° C., in the presence or absence of catalytic amounts of N,N-dimethylformamide, pyridine or 4-dimethylaminopyridine, and the mixture is heated at from 70° to 100° C. for from 3 to 6 hours, after which the nitrobenzoyl chloride has been formed and, if necessary, excess thionyl chloride can be distilled out. The Friedel-Crafts acylation is then carried out by addition of catalytic amounts of Lewis acid as explained above.

The process according to the invention can be carried out either continuously or batchwise, and it is possible to dispense with the use of inert solvents. At the same time, the novel process is very simple to carry out, and the required products are obtained in high yield and purity.

The nitrobenzophenones of the formula I are valuable intermediates for the preparation of azo dyes.

Conversion of the nitrobenzophenone I by conventional methods, eg. by catalytic hydrogenation, into the corresponding aminobenzophenones of the formula Ia

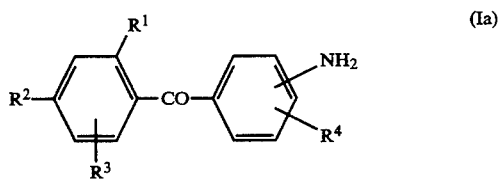

where $R^1$, $R^2$, $R^3$ and $R^4$ each has the abovementioned meanings, results in valuable diazo components for preparing azo dyes as disclosed, for example, in DE-A 2 001 821 or DE-A 2 157 229.

The present invention also relates to a color-stable modification of the dye of the formula IV

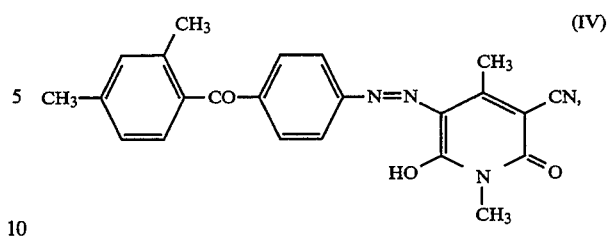

whose X-ray diffraction diagram (Cu-$K_g$ radiation) has the following lines of strong intensity at diffraction angles $\theta$ [°] of 8.085, 12.772, 13.644, 24.864 and 25.656, lines of moderate intensity at diffraction angles $\theta$ [°] of 16.402, 18.894, 20.822, 21.940, 27.546 and 28.256, and lines of weak intensity at diffraction angles $\theta$ [°] of 14.490, 15.352 and 23.711.

The color-unstable modification of the dye of the formula IV has an X-ray diffraction diagram (Cu-$K_g$ radiation) with the following lines of strong intensity at diffraction angles $\theta$ [°] of 8.407, 12.821 and 25.231, lines of moderate intensity at diffraction angles $\theta$ [°] of 13,822, 21.921, 25,865 and 26,547 and lines of low intensity at diffraction angles $\theta$ [°] of 15,404, 16.641 and 27,579.

The X-ray diffraction diagrams were recorded in each case using a Siemens type D 5000 powder diffractometer.

The dye of the formula IV is disclosed in DE-A 2 157 229. No preparation process is described therein. However, if the dye is produced by the method specified in DE-A 2 001 821, namely by diazotization of 4-amino-2',4'-dimethylbenzophenone in 30% by weight hydrochloric acid with sodium nitrite and subsequent coupling with 1,4-dimethyl-3-cyano-2-hydroxy-6-pyridone, the resulting modification has inadequate stability under the conventional dyeing conditions.

The color-unstable modification of the dye IV can be converted into the color-stable modification by treatment with aqueous alkali at pH 7-9 at from 20° to 90° C. for from half an hour to four hours.

It is also possible to produce the color-stable modification directly in the synthesis of the dye. This can be achieved by carrying out the coupling reaction (reaction of the diazonium salt of 4-amino-2',4'-dimethylbenzophenone with 1,4-dimethyl-5-cyano-2-hydroxy-6-pyridone) at a pH of from 7 to 10.5.

The novel color-stable modification of the dye of the formula IV is advantageously suitable for dyeing or printing synthetic fiber material, for example polyester fabric.

Dyeings in a deep yellow shade with a high degree of exhaustion and very good lightfastness and fastness to heat setting and pleating are obtained.

The examples illustrate the invention.

EXAMPLE 1 a) 210 ml of m-xylene were mixed with 167 g of p-nitrobenzoic acid. Small amounts of water which had been introduced with the p-nitrobenzoic acid were removed azeotropically with a water trap. The mixture was then cooled to 70° C., 1 g of N,N-dimethylformamide was added and then, at 70°–75° C., 88 ml of thionyl chloride were added. The mixture was stirred at 80°–85° C. for 3 hours to produce a solution of p-nitrobenzoyl chloride in m-xylene. This solution was freed of thionyl chloride by distilling out a small amount of m-xylene.

b) The mixture was then cooled to room temperature and 17 g of anhydrous aluminum chloride powder were added. The mixture was heated to 100°–110° C. over the course of 1.5 hours, during which hydrogen chloride was evolved, and the mixture was stirred at this temperature for 3 hours until the evolution of hydrogen chloride stopped. The mixture was cooled to 90° C. and decomposed in 600 ml of water. Excess m-xylene was then removed by steam distillation, 0.5 g of an acidic wetting agent was added to the residue, and the mixture was cooled to room temperature while stirring. Filtration with suction, washing with water and drying resulted in 255 g of the benzophenone of the formula

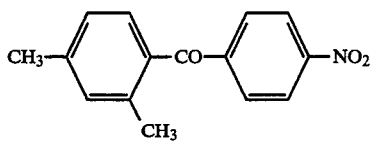

$H^1$-NMR (DMSO-$D_6$) [ppm]
8.35 (d 2)
7.99 (d 2)
7.28
7.25
7.14
2.38 (s 3)
2.30 (s 3)

The recovered m-xylene was pure. It can be reused for further reactions.

c) The 4-nitro-2',4'-dimethylbenzophenone obtained in b) was mixed with 900 ml of isobutanol and 3.5 g of activated nickel powder and hydrogenated under a slight superatmospheric pressure (1.25 bar) of hydrogen at 50°–60° C. to give 4-amino-2',4'-dimethylbenzophenone. The catalyst was filtered off and then the organic solvent was distilled off to recover it, and water at 95° C. was added to the residue at 100°–110° C. and the mixture was stirred until room temperature was reached. 4-Amino-2',4'-dimethylbenzophenone crystallized out at 90° C. The crystalline product was filtered off with suction, washed with water and dried. 215 g of amino compound (melting point 121° C.) were obtained.

$H^1$-NMR (DMSO-$D_6$) [ppm]
7.40 (d 2)
7.15 (s 1)
6.97 (s 1)
6.55 (d 2)
6.21 (s 2-$NH_2$)
2.29 (s 3-$CH_3$)
2.09 (s 3-$CH_3$)

d) 226 g of 4-amino-2',4'-dimethylbenzophenone were dissolved at 50°–60° C. in 350 ml of 27% by weight sulfuric acid. Then 450 ml of 5 N hydrochloric acid and 2 g of an acidic wetting agent were added, and the mixture was stirred in the cold to precipitate the amino component as crystals of the hydrochloride. Then, at 0°–7° C., 320 ml of 23% by weight aqueous sodium nitrite solution were added, and the resulting cloudy diazoniumsalt solution was stirred at 0°–5° C. for 2.5 hours. Excess nitrous acid was then decomposed with sulfamic acid. The reaction mixture was added to a mixture prepared as follows:

164 g of 1,4-dimethyl-5-cyano-2-hydroxy-6-pyridone were dissolved in 2000 ml of water and sodium hydroxide solution at pH 7.5. The solution was cooled to 0° C. by adding ice and 20 g of sodium carbonate were added.

During the addition of the diazonium salt, dilute sodium hydroxide solution was added simultaneously so that the pH of the mixture was maintained in the range from 6 to 9. The coupling was rapidly completed after addition of the diazonium salt. The pH was adjusted to 7.5–8.0, and the mixture was stirred for 1.5 hours and then heated at this pH to 85°–95° C. and maintained at this for 45 minutes. The dye suspension was then filtered, and the material on the filter was washed with water until free of salts and was dried.

The resulting dye of the formula

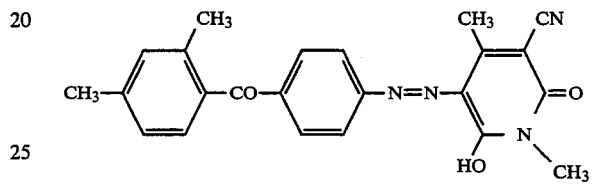

melts at 183° C.

It has the following X-ray spectrum: diffraction angles θ [°] of 8,085, 12.772, 13,644, 24,864 and 25,656, lines of moderate intensity at diffraction angles θ [°] of 16.402, 18,894, 20,822, 21.940, 27.546 and 28,256 and lines of weak intensity at diffraction angles θ [°] of 14,490, 15,352 and 23.711.

e) 45 g of the dye obtained in d) were converted into a paste with 45 g of dispersant based on a naphthalenesulfonic acid-formaldehyde condensate, which is described as dispersant 3 in EP-A-463 401, the solids content was adjusted to 35% by weight with water, and the mixture was ground at pH 8.5 in a sand mill until a satisfactory fine distribution was reached. The dispersion was spray-dried with the inlet air at 120° C. and was adjusted to the final color strength by adding 10 g of the abovementioned dispersant.

The resulting dye powder has the fine distribution achieved in the grinding stage and is very suitable for dyeing polyester fibers and polyester/cotton blend fabrics.

In particular when dyeing packages of wound yarns of textured polyester fibers, there were no dye deposits or unlevelness at all.

EXAMPLE 2

226 g of 4-amino-2',4'-dimethylbenzophenone were diazotized as in Example 1. However, a solution of 164 g of 1,4-dimethyl-5-cyano-2-hydroxy-6-pyridone and 50 g of sodium acetate in 2000 ml of water (pH about 4) was used for the coupling reaction. The diazoniumsalt mixture was then run into the pyridone so that the pH of the resulting mixture was always in the range from 3.5 to 5.5.

The reaction was rapidly complete. The precipitated dye melts at about 70° C. and therefore cannot be converted into a high-melting form by heat treatment. However, if the pH of the resulting reaction mixture is adjusted to 8 with sodium hydroxide solution, and the suspension is stirred at room temperature for 4 hours and then heated as described in Example 1, the high-melting form is obtained.

EXAMPLE 3 a) 200 ml of p-xylene were mixed with 167 g of p-nitrobenzoic acid, and water was removed from the mixture by azeotropic distillation with a water trap. The mixture was then cooled to 70° C., 1 g of N,N-dimethylformamide was added and then, at 70°–75° C., 88 ml of thionyl chloride were added dropwise, and the mixture was stirred at 80°–85° C. for 3 hours. The resulting solution of p-nitrobenzoyl chloride in p-xylene was freed of thionyl chloride by distilling out a small amount of p-xylene.

b) The mixture was then cooled to room temperature, 17 g of anhydrous aluminum chloride powder were added and the mixture was heated to 110° C. over the course of 1.5 hours. Evolution of hydrogen chloride ceased after stirring at this temperature for 3 hours. The mixture was then cooled to 90° C. and decomposed with 600 ml of water. Excess p-xylene was then completely removed by steam distillation, 0.5 g of an acidic wetting agent was added to the residue, and the mixture was cooled to room temperature while stirring. The precipitated product was filtered off with suction and washed with water. Drying resulted in 225 g of the benzophenone of the formula

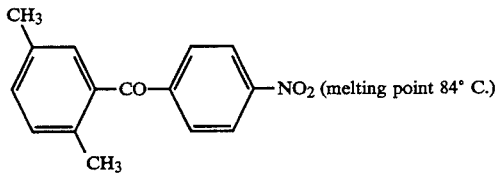 (melting point 84° C.)

H$^1$-NMR (DMSO-D$_6$) [ppm]
8.36 (d 2)
7.91 (d 2)
7.31 (4)
7.17 (s 1)
2.29 (s 3)
2.22 (s 3)

c) 4-Nitro-2′,5′-dimethylbenzophenone was reduced to 4-amino-2′,5′-dimethylbenzophenone as in Example 1. 215 g of a product with a melting point of 149° C. were obtained.

H$^1$-NMR (DMSO-D$_6$) [ppm]
7.41 (d 2)
7.08 (d 3)
6.56 (d 2)
6.20 (2, NH)
2.32 (s 3)
2.12 (s 3)

d) 226 g of 4-amino-2′,5′-dimethylbenzophenone were dissolved in 75 g of sulfuric acid and 300 ml of water with 2 g of acidic wetting agent with heating. To this were added 800 ml of 5 N hydrochloric acid, and the mixture was cooled to room temperature, also adding 100 ml of glacial acetic acid.

The resulting suspension was cooled to 0°–7° C. and 320 ml of 23% by weight aqueous sodium nitrite solution were added, and the mixture was stirred at 0°–5° C. for 3 hours. Excess nitrous acid was decomposed, and the reaction mixture was added as described in Example 1 to a mixture prepared as in Example 1 and containing 206 g of 1-butyl-4-methyl-5-cyano-2-hydroxy-6-pyridone.

The workup described in Example 1 resulted in 440 g of a yellow dye powder which melts at 151° C. and dyes polyester fabric with a deep yellow hue.

EXAMPLE 4

A mixture of 127 g of m-xylene (anhydrous) and g of p-nitrobenzoyl chloride was mixed with 3 g of anhydrous iron(III) chloride and then heated to 90°–100° C., when hydrogen chloride was evolved. The mixture was stirred at 90°–100° C. for 5 hours and then the melt was stirred with 450 ml of water and the excess m-xylene was removed by steam distillation. 1 g of an acidic wetting agent was added, and the mixture was cooled to room temperature, so that 4-nitro-2′,4′-dimethylbenzophenone crystals separated out. Filtration with suction, washing and drying resulted in 253 g of the benzophenone of the formula

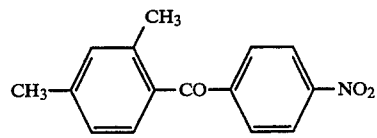

in pure form.

We claim:

1. A process for preparing nitrobenzophenones of the formula I

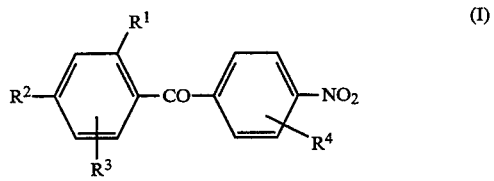 (I)

wherein $R^1$ and $R^2$ are identical or different and each independently of one another is $C_{1-4}$ alkyl, $R^3$ is hydrogen and $R^4$ is hydrogen or halogen, by reacting aromatic compounds of the formula II

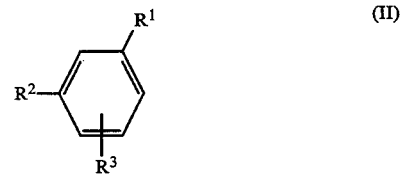 (II)

wherein $R^1$, $R^2$ and $R^3$ each have the above-mentioned meanings, with nitrobenzoyl chloride of the formula III

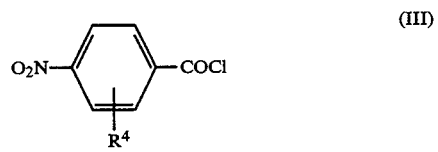 (III)

wherein $R^4$ has the above mentioned meanings, in the presence of a Lewis acid, wherein the reaction is carried out essentially in the absence of inert solvents at from 50°–110° C. and with a molar ratio of aromatic compound of the formula II to nitrobenzoyl chloride of the formula III of from 1:1 to 2:1, and 0.5–20% by weight of iron (III) chloride based on said aromatic compound of the formula II is used as said Lewis acid.

2. A process as claimed in claim 1, wherein the reaction is carried out with a molar ratio of aromatic compound II to nitrobenzoyl chloride III of from 1.1:1 to 1.3:1.

3. A process as claimed in claim 1, wherein $R^1$ and $R^2$ are each methyl and $R^3$ is hydrogen.

4. A process as claimed in claim 1, wherein p-nitrobenzoyl chloride is reacted.

5. The process of claim 1, wherein said reaction is carried out at from 50°–90° C.

6. The process of claim 1, wherein said reaction is conducted for from 3–6 hours.

7. The process of claim 1, wherein said molar ratio of aromatic compound of the formula II to nitrobenzoyl chloride of the formula III is from 1.1:1 to 1.3:1.

8. The process of claim 1, wherein 2–8% by weight of said Lewis acid is used based on said aromatic compound of the formula II.

9. The process of claim 1, wherein said reaction is carried out in the presence of up to 10% by weight, based on the weight of said aromatic compound of the formula II, of an inert solvent.

10. The process of claim 1, wherein said reaction is carried out in the presence of up to 5% by weight, based on the weight of said aromatic compound of formula II, of an inert solvent.

11. The process of claim 1, wherein said reaction is carried out in the complete absence of an inert solvent.

* * * * *